(12) United States Patent
Evans et al.

(10) Patent No.: US 6,714,879 B2
(45) Date of Patent: Mar. 30, 2004

(54) CLOSED LOOP RHEOMETER

(75) Inventors: Nigel Evans, Oxon (GB); John Wilkinson, Gloucester (GB)

(73) Assignee: Bohlin Instruments Limited, Gloucester (GB)

( * ) Notice: Subject to any disclaimer, the term of this patent is extended or adjusted under 35 U.S.C. 154(b) by 131 days.

(21) Appl. No.: 10/024,437

(22) Filed: Dec. 18, 2001

(65) Prior Publication Data

US 2002/0138215 A1 Sep. 26, 2002

(30) Foreign Application Priority Data

Dec. 19, 2000 (GB) ............................................. 0031022

(51) Int. Cl.[7] ............................................. G06F 19/00
(52) U.S. Cl. ........................................ 702/50; 73/54.01
(58) Field of Search .............................. 702/42, 43, 50; 73/847, 54.31, 54.01, 54.04, 54.37

(56) References Cited

U.S. PATENT DOCUMENTS 4,501,155 A * 2/1985 Garritano ..................... 73/847
5,321,974 A * 6/1994 Hemmings et al. ........ 73/54.31

* cited by examiner

Primary Examiner—John Barlow
Assistant Examiner—Stephen J. Cherry
(74) Attorney, Agent, or Firm—Lahive & Cockfield LLP; Anthony A. Laurentano

(57) ABSTRACT

The invention provides a method for operating a controlled stress rheometer in a controlled strain mode to follow a demand strain $X_d$ in a sample having applied thereto a variable demand force $T_d$, inducing an actual strain X including the steps of:

monitoring the actual strain X;
  continuously comparing the actual strain X with the demand strain $X_d$ and calculating the difference;
  calculating in real time, using an appropriate algorithm, the value of $T_d$ necessary to adjust the strain from X to $X_d$, and
  adjusting $T_d$ to the calculated value so as to effect this strain adjustment. The method may be performed by a computer software algorithm installed in a digital signal processor forming part of the controller system of the rheometer.

15 Claims, 3 Drawing Sheets

CLOSED LOOP RHEOMETER

This invention relates to rheometers. In particular the invention relates to a method for controlling the strain and measurement force of a rheometer.

A typical rheometer comprises at least two bounding surfaces, one or more of which may be moveable by rotation or other means, between which a material whose viscosity or other visco-elastic property is to be measured is positioned. Movement of the moveable surface or surfaces may be controlled, for example by a microprocessor embodied in the rheometer apparatus. Associated with the apparatus are a force actuator for applying a known force to the sample via the one or more moveable surfaces and a position transducer which records displacement of a sample under test and hence the strain which it has undergone for a given applied force.

Two modes of operation are typically possible; firstly open-loop mode, whereby the sample under test is subjected to a known force by the force transducer, secondly closed loop mode, where the sample under test is subjected to a controlled strain by regulation of the torque transducer. By suitable selection of a bearing suspension system (for example, a low friction air bearing or a mechanical bearing with known frictional properties), the first mode of operation can be optimised and the rheometer is thus sometimes termed a 'controlled stress' rheometer. In such a controlled stress rheometer, the force or stress is controllable with high accuracy so that the strain may be measured. The second mode of operation is sometimes termed 'controlled strain'. In this mode, the force becomes the measured variable.

Movement of the moveable surface or surfaces is typically effected by one of two types of motor; an electrically commutated (EC) motor or a purely inductive motor. The latter are a relatively recent development in rheometer design and dispense with the conventional use of permanent magnets. These designs have an extremely low moment of inertia and can respond quickly when required to accelerate or change position. The former, which are sometimes referred to as brushless DC motors, rely upon permanent magnets placed within the rotor in order to work. This renders them relatively heavy in terms of their inertia and results in that, for a given force, they take longer to accelerate or change position, thereby fundamentally limiting their transient response. Whilst, inductive motors generally out perform EC motors, EC motors are relatively inexpensive to produce and are still in common use.

As described in "Real Controlled Stress and Controlled Strain Experiments With The Same Rheometer"; XIIIth International Congress on Rheology, Cambridge 2000; Lauger and Huck, Physica Messtechnik GmbH have developed an EC motor-based rotational rheometer which incorporates a controller system which enables the strain induced in a sample to be controlled as well as or instead of the applied force. The controller utilises knowledge of the rotor field to adjust the mechanical torque in such a way that it is linear to the total amount of the stator current, whereby a change in the stator current is followed by an almost instantaneous change in the torque. The presetting and measurement of the corresponding properties are done from the same side of the rheometer, thereby avoiding the need for additional transducers. As a result, the rheometer can be operated as a strain actuator and a stress transducer.

A downfall of the Physica system is that it requires the user to adjust the gain on the controller manually via software constants. Thus the Physica system is not fully adaptive and cannot be fully automated.

In a first aspect the present invention provides a method for operating a controlled stress rheometer in a controlled strain mode to follow a demand strain $X_d$ in a sample having applied thereto a variable demand force $T_d$, inducing an actual strain X including the steps of:

monitoring the actual strain X;

continuously comparing the actual strain X with the demand strain $X_d$ and calculating the difference;

calculating in real time, using an appropriate algorithm, the value of $T_d$ necessary to adjust the strain from X to $X_d$; and adjusting $T_d$ to the calculated value so as to effect this strain adjustment.

The method may be implemented in software on a digital signal processor incorporated into the control system of the rheometer. The digital signal processor is configured to output a digital representation of the demand force $T_d$ this output may be converted, via a digital to analogue converter, to an analogue signal which may be used to control the force actuator of the rheometer. The output of the position transducer of the rheometer is similarly converted to a digital representation of the strain X by a resolver to digital converter and the resulting digital data is input to the digital signal processor. A closed loop algorithm within the digital signal processor calculates the appropriate adjustment to $T_d$ and relays this to the force actuator.

A suitable algorithm may utilise a transfer function based on the third order solution to the Butterworth approximation typically represented as:

$$H(S) = \frac{W^3}{S^3 + S^2(1+2Z)W + S(1+2Z)W^2 + W^3}$$

where w is the corner frequency of the function and the controller bandwidth, z is the damping factor and s is the Laplace operator. Values for w and z are determined from:

$K_i = Iw^3$ $K_d = (1+2z)Iw - C$ $K_p = (1+2z)Iw^2$ where Kd, $K_i$ and $K_p$ are controller coefficients. C=the coefficient of friction of the rheometer and I=the inertia of the system.

The coefficient of friction and the stiffness of the sample under test will affect the response of the system. However, it has been found in practice that a controller operating in accordance with the invention will give a response close to the third order Butterworth characteristic over a wide range of variation in system coefficient of friction, C. For samples with a low stiffness, however, the stability of the system may be reduced. Preferably, therefor, this is compensated for by reducing all the controller coefficients, $K_i$, $K_d$ and $K_p$ by a proportionate amount, whilst maintaining a reasonably low controller bandwidth, w. In this way, values may be found for the controller coefficients that permit the controller response to be stable yet effective for a wide range of materials under test.

Some potential applications of apparatus employing the method of the invention may require both high controller bandwidth and high controller stability when used in relation to samples with low stiffness and high coefficients of friction. In such applications, limiting the controller bandwidth and thereby reducing the overall gain can permit stable controller operation.

Some applications may require a higher controller bandwidth than can be achieved as above. In such cases, the effective bandwidth of the controller may be increased by adapting the controller coefficients dynamically. One method for achieving this is to compare the measured response of the controller with the output of a reference model of the preferred system response, such as the third order Butterworth approximation, previously referred to. The difference between the measured controller response, X, and a reference model output estimate, X, may then be used as a parameter to recalculate the controller coefficients dynamically, in order to force the controller response to follow the reference model output more closely.

Another potential application of apparatus incorporating a controller operating in accordance with the present invention is as a compliance free torque measuring device. In such an embodiment, a separate actuator may be used on the opposing surface of the rheometer to effect a deformation in the sample. Other applications may utilise two rheometers operated in accordance with the invention, their moveable surfaces being opposed to each other with the sample between them.

In a second aspect, the present invention provides a method for operating a controlled stress rheometer as a torque measuring device to follow a variable demand force $T_d$ in a sample subjected to a pre-selected demand strain $X_d$ including the steps of:

monitoring the actual strain X;

continuously comparing the actual strain X with the demand strain $X_d$ and calculating the difference;

adjusting the actual strain X to equal the demand strain $X_d$, calculating in real time, using an appropriate algorithm, the value of $T_d$ necessary to adjust the strain from X to $X_d$.

The term "pre-selected" in the context of this aspect of the invention includes a constant demand strain and a demand strain which is varied according to a pre-selected strain profile The methods of the invention may be performed using a rheometer with an EC motor or a purely inductive motor. Preferably, the motor is fully inductive as this provides the additional technical benefits mentioned above.

For the purposes of exemplification some embodiments of the invention will now be more clearly described with reference to the following Figures in which.

Figure 1:
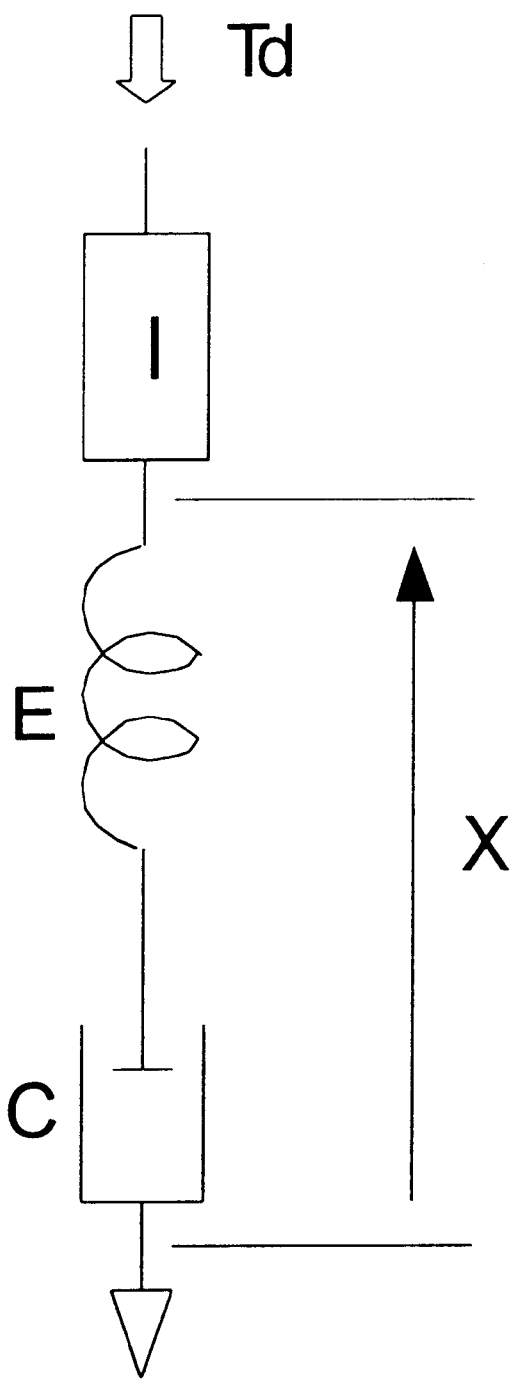
FIG. 1 illustrates the basic principle behind a controlled stress rheometer as is well known in the prior art.

The basic principle of operation of a controlled stress rheometer is illustrated in FIG. 1. A demand force, $T_d$ is applied by a force actuator. The force $T_d$ operates on the inertia of the system, I, and is transmitted through the stiffness, E, and coefficient of friction, C of the system, including the sample under test. The application of the force results in a change in the strain of the sample under test. The amount of strain is determined by measuring the change in displacement, X, of the sample using a position transducer.

Figure 2:
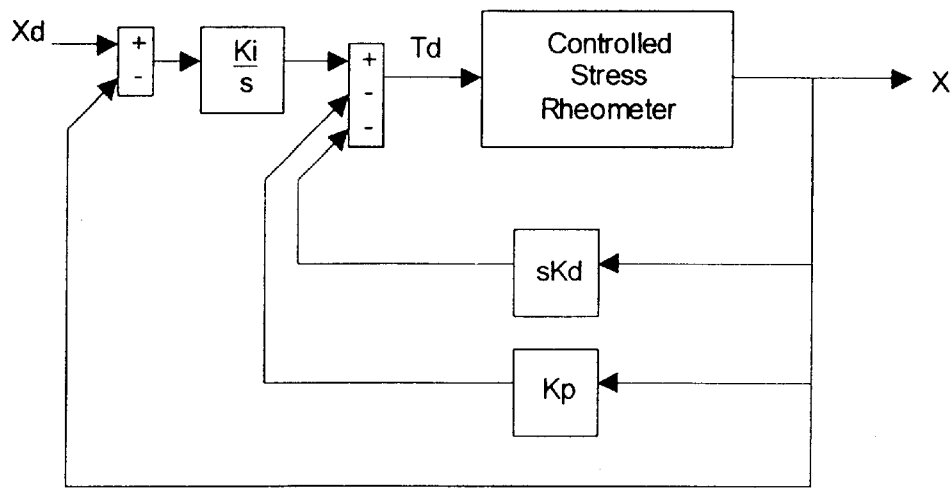
FIG. 2 illustrates schematically the control loop of a controller for controlling strain in a controlled stress rheometer in accordance with the present invention.

The purpose of the control loop is to adjust the demand force, $T_d$, input to the controlled stress rheometer in order to constrain the strain output, X, to follow the demand strain input, $X_d$, of the system. The transfer function of the controlled stress rheometer of FIG. 1 may be combined with the control loop shown in FIG. 2 to provide the overall transfer function of the strain controller. $K_i$ and $K_p$ are controller parameters and $K_d$ is the controller coefficient is discussed above.

S is the Laplace operator for the controlled stress rheometer of FIG. 1.

Figure 3:
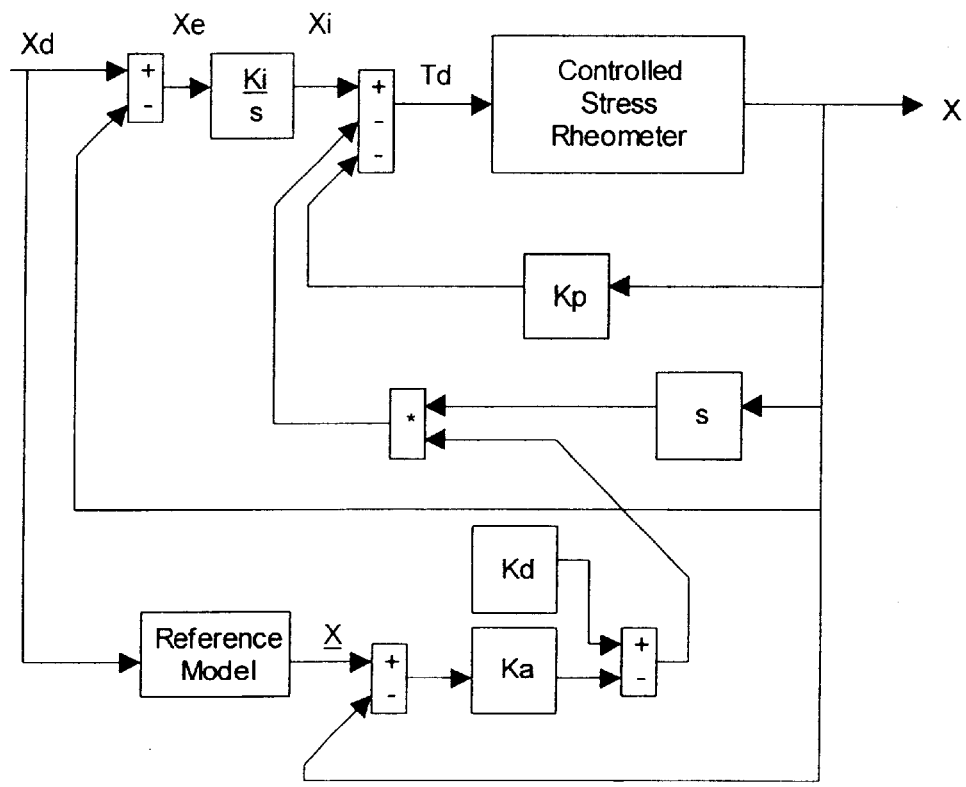
FIG. 3 illustrates schematically the control loop of a controller for adaptively controlling strain in a controlled stress rheometer in accordance with the present invention.

In the adaptive strain controller system shown in FIG. 3, the coefficient $K_a$ is the coefficient of adaption of the controller. An appropriate value of $K_a$ may be determined empirically for a particular controller arrangement. The value of $K_a$ is selected to be high enough to provide sufficient improvement in the effective bandwidth of the controller, and low enough so as not to degrade the stability of the controller. Adaptation is achieved by reducing the controller coefficient $K_d$ in proportion to the difference between the measured controller response and the reference model output as illustrated.

Figure 4:
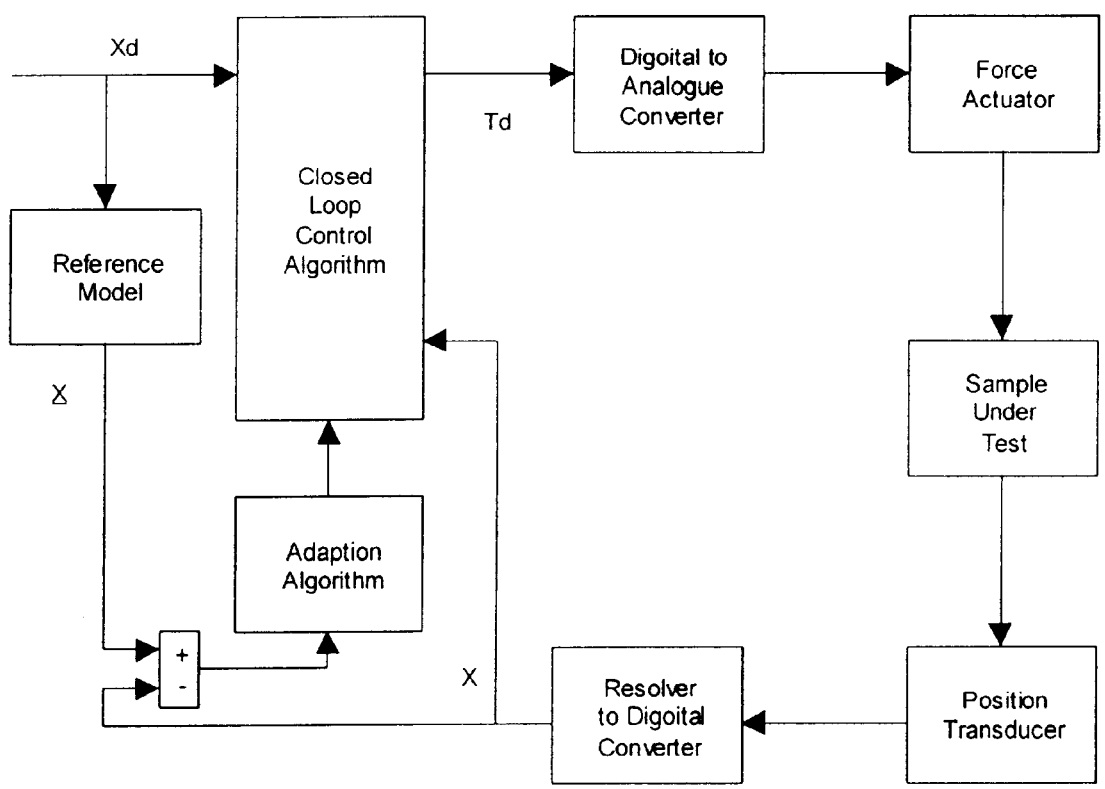
FIG. 4 illustrates schematically in a general arrangement, apparatus for performing the present invention.

An adaptive closed loop control algorithm is shown in FIG. 4. The difference between the measured controller response, X, and the reference model output estimate, X, is used as a parameter to recalculate the controller coefficients dynamically, in order to force the controller response to follow the reference model output as described above.

It will be appreciated from the foregoing that the method of the present invention when used to control the operation of a controlled stress rheometer, permits that rheometer to be used in at least two additional modes; firstly, the spindle can be used as a controlled strain actuator and secondly, it can be used as a force or torque measuring device when the strain is held constant or altered as prescribed by the controller. Each of these modes can be combined with a single rheological measurement and more importantly, the actuator function and torque measurement can be combined into a single measurement spindle.

It is to be understood that the foregoing represents just some embodiments of the invention. Other embodiments of the invention will occur readily to the skilled reader without the need to apply inventive thought.

What is claimed is:

1. A method for operating a controlled stress rheometer in a controlled strain mode to follow a demand strain $X_d$ in a sample having applied thereto a variable demand force $T_d$ inducing an actual strain X including the steps of:

monitoring the actual strain X;

continuously comparing the actual strain X with the demand strain $X_d$ and calculating the difference; and calculating in real time, using an appropriate algorithm, the value of $T_d$ necessary to adjust the strain from X to $X_d$; and adjusting $T_d$ to the calculated value so as to effect this strain adjustment, wherein the algorithm employs a transfer function based on a third order solution to the Butterworth approximation.

2. A method as claimed in claim 1, wherein the transfer function is $$H(S) = \frac{W^3}{S^3 + S^2(1+2Z)W + S(1+2Z)W^2 + W^3}$$

where w is the corner frequency of the function and the controller bandwidth, z is the damping factor and s is the Laplace operator and wherein values for w and z are selected to give a desired frequency response and:

$K_i = Iw^3$ $K_d = (1+2z)Iw - C$ $K_p=(1+2z)Iw^2$ where Kd, $K_i$ and $K_p$ are controller coefficients.

C=the coefficient of friction of the rheometer and I=the inertia of the system.

3. A controller for controlling a controlled stress rheometer in a controlled strain mode, the controller comprising a digital signal processor programmed to perform the method as claim in claim 2.

4. A controller for controlling a controlled stress rheometer in a controlled strain mode, the controller comprising a digital signal processor programmed to perform the method as claimed in claim 1.

5. A controller as claimed in claim 4 wherein the digital signal processor p further comprises a digital to analogue converter configured to communicate with a force actuator of the rheometer and a resolver to digital converter configured to communicate with a position transducer of the rheometer.

6. A controller as claimed in claim 5 wherein the digital signal processor is further programmed with an adaption algorithm configured to calculate the difference between the actual strain, X, and a reference model output estimate, X, and use this difference as a parameter to recalculate the controller coefficients dynamically and thereby force the controller response to follow the reference model output.

7. A controlled stress rheometer comprising a controller as claimed in claim 6.

8. A controlled stress rheometer comprising a controller as claimed in claim 5.

9. A controlled stress rheometer comprising a controller as claimed in claim 4.

10. A controlled stress rheometer as claimed in claim 9 wherein the rheometer comprises an electrically commutated motor.

11. A controlled stress rheometer as claimed in claim 9 wherein the rheometer comprises a purely inductive motor.

12. A controller for controlling a controlled stress rheometer in a controlled strain mode, the controller comprising a digital signal processor programmed to perform the method as claimed in claim 1.

13. A method for operating a controlled stress rheometer as a torque measuring device to follow a variable demand force $T_d$ in a sample subjected to a pre-selected demand strain $X_d$, said method comprising the steps of:

monitoring the actual strain X;

continuously comparing the actual strain X with the demand strain $X_d$ and calculating the difference;

adjusting the actual strain X to equal the demand strain $X_d$, and calculating in real time, using an appropriate algorithm, the value of $T_d$ necessary to adjust the strain from X to $X_d$.

wherein the algorithm employs a transfer function based on a third order solution to the Butterworth approximation.

14. A controller for controlling the operation of a controlled stress rheometer as a torque measuring device, the controller comprising a digital signal processor programed to perform the method as claimed in claim 13.

15. A controlled stress rheometer comprising a controller as claimed 14.

* * * * *